(12) United States Patent
Darr

(10) Patent No.: US 7,704,234 B2
(45) Date of Patent: Apr. 27, 2010

(54) DYNAFLEX

(76) Inventor: Allan J. Darr, 2454 General Potter Hwy., Centre Hall, PA (US) 16828

( * ) Notice: Subject to any disclaimer, the term of this patent is extended or adjusted under 35 U.S.C. 154(b) by 159 days.

(21) Appl. No.: 11/784,142

(22) Filed: Apr. 5, 2007

(65) Prior Publication Data

US 2008/0249436 A1    Oct. 9, 2008

(51) Int. Cl.
*A61M 5/178* (2006.01)
(52) U.S. Cl. .................................. 604/164.01
(58) Field of Classification Search ............. 604/164.1, 604/525, 528; 600/564
See application file for complete search history.

(56) References Cited

U.S. PATENT DOCUMENTS

| | | | | |
|---|---|---|---|---|
| 3,893,445 | A * | 7/1975 | Hofsess | 600/567 |
| 4,100,393 | A * | 7/1978 | Luther | 219/121.71 |
| 4,377,165 | A * | 3/1983 | Luther et al. | 604/160 |
| 4,401,433 | A * | 8/1983 | Luther | 604/159 |
| 4,449,973 | A * | 5/1984 | Luther | 604/161 |
| 5,273,051 | A | 12/1993 | Wilk | |
| 5,336,191 | A | 8/1994 | Davis | |
| 5,601,588 | A | 2/1997 | Tonomura | |
| 5,971,957 | A * | 10/1999 | Luther et al. | 604/160 |
| 6,015,391 | A | 1/2000 | Rishton | |
| 6,371,943 | B1 | 4/2002 | Racz | |
| 6,419,641 | B1 | 7/2002 | Mark | |
| 6,723,082 | B1 * | 4/2004 | Payne et al. | 604/528 |
| 7,048,694 | B2 | 5/2006 | Mark | |
| 7,063,703 | B2 * | 6/2006 | Reo | 606/79 |
| 7,101,361 | B2 | 9/2006 | Gardeski | |
| 7,128,956 | B2 | 10/2006 | Wang | |
| 7,147,607 | B2 | 12/2006 | Wang | |
| 7,204,812 | B2 | 4/2007 | Wang | |
| 2002/0026202 | A1 * | 2/2002 | Honey et al. | 606/127 |
| 2004/0133124 | A1 * | 7/2004 | Bates et al. | 600/564 |
| 2005/0256425 | A1 * | 11/2005 | Prusiner | 600/567 |
| 2007/0010843 | A1 * | 1/2007 | Green | 606/185 |
| 2008/0103411 | A1 * | 5/2008 | Van Bladel et al. | 600/564 |

OTHER PUBLICATIONS

PCT International Search Report and Written Opinion of the International Searching Authority for PCT/US08/03986, Jul. 25, 2008, ProAct, Ltd.

* cited by examiner

*Primary Examiner*—Nicholas D Lucchesi
*Assistant Examiner*—Diva Ranade
(74) *Attorney, Agent, or Firm*—McQuaide, Blasko, Fleming & Faulkner, Inc.

(57) ABSTRACT

Utilizing the technology and methods disclosed, the characteristics of flexibility and rigidity for intralumenal devices, including coaxial two piece devices such as stylet and needle sets, can be adapted by the physician or device manufacturer according to the type of procedure, the patient size and unique anatomical challenges of a given procedure. Rigidity and flexibility can be actively controlled by the operator at predefined portions of a device through rotating the stylet within the cannula to bring about alignments of customized notches to impart target flexibility or rigidity profiles at specific spots on the device. The device operator may alter the relationship and orientation of specific notched and non-notched segments of either or both the stylet and cannula that are strategically located at said critical points along the length of the device.

11 Claims, 6 Drawing Sheets

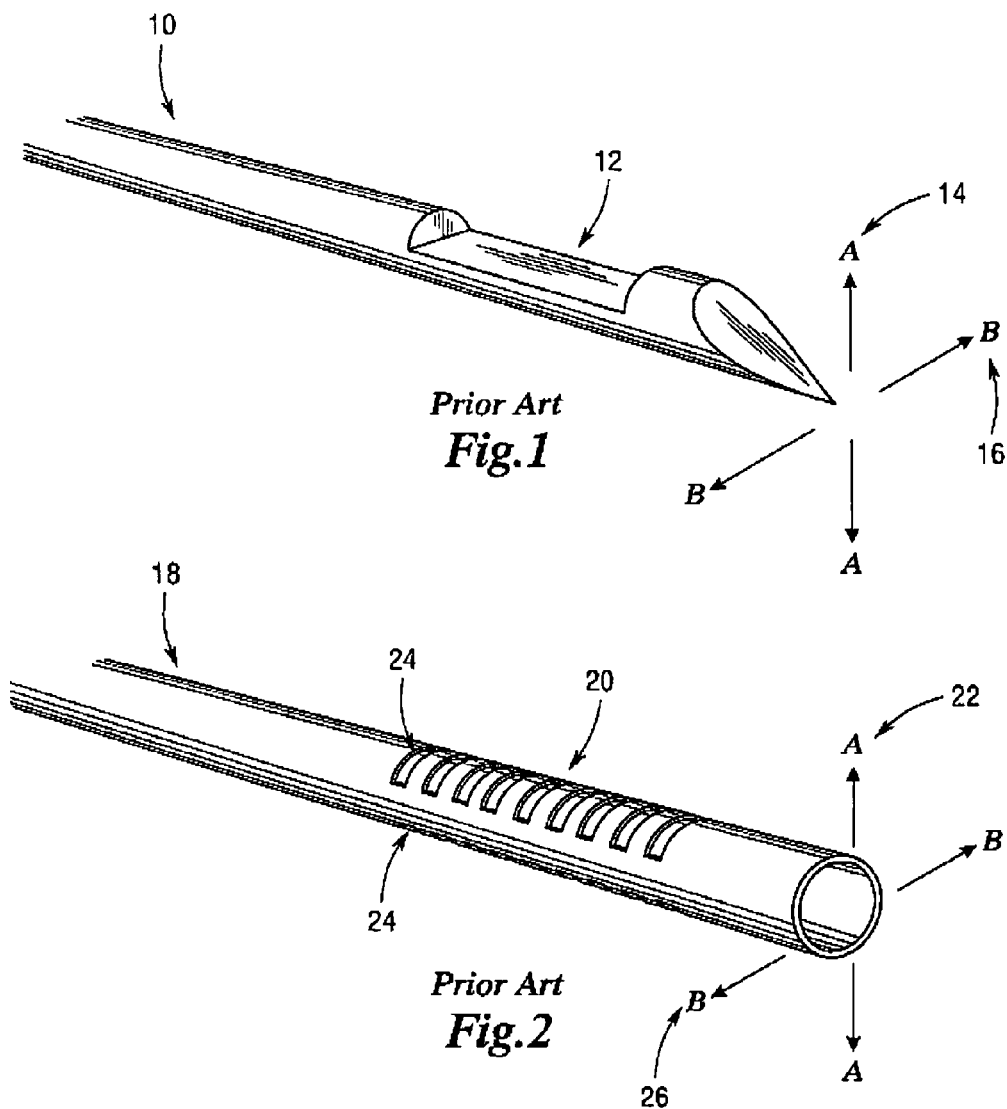

DYNAFLEX

BACKGROUND OF THE INVENTION

1. Field of the Invention

The field of the invention is intralumenal medical devices, and specifically, including coaxial two-piece devices, such as stylet and needle set devices, which devices exhibit enhanced performance through inherently tunable flexibility and rigidity profiles.

2. Background Art

Numerous devices have been developed to address the recurring issue of maximizing the mechanical properties of a catheter or other medical access device to be advanced through a lumen. One such key property is generally referred to in the art as "pushability," a term used to describe the rigidity of a device and its ability to advance through a lumen. See as an example U.S. Pat. No. 7,022,106. Another such property is the flexibility of a device. It is desirable for a device to be flexible enough to allow the device to traverse contorted/curved scopes and passages in the body. At the same time, the tip rigidity allows the device to better penetrate tissue and the "pushability" allows proximal force transmission to the distal tip. Most composite materials provide for the flexibility needs, but do not meet the tip rigidity and pushability needs. Stainless steel provides very good rigidity and pushability, but is very limited in terms of flexibility.

Accordingly, companies have utilized various machining techniques in an attempt to impact these key properties. Current patents and technology have employed relief notches in both stylets and cannula tubing in an effort to increase flexibility. One example of such "static" flexibility is described in U.S. Patent Publication No. 2004/133124, to Bates, et al. Bates discloses a cannula and a stylet with notches designed to increase flexibility, but only in one plane of operation. However such notching does not allow for custom or adjustable flexibility and rigidity that is required in many medical procedures. As a result, such a device is flexible only in a fixed or constant, or a "static" manner, and is thus of limited usefulness.

As one example of desired dynamic flexibility in certain procedures, it is necessary with some procedures that the distal tip section initially be more flexible in order to accommodate tip deflection of a scope/introducer. As the device tip protrudes from the scope/introducer, it could be made more rigid, while at the same time the subsequent distal section is made more flexible to accommodate passage through the deflected scope/introducer. Under current art and designs, there is no method or device that will allow for this real-time modification and/or adaptation of flexibility. Such "tunable flexibility" features that are variable, adjustable and dynamic have broad application for endoscopic, bronchoscopic and laparoscopic procedures. Such a technology could also be applied to intravascular, neurosurgery, optical procedures and a broad range of minimally invasive surgical procedures.

For instance, certain procedures require the device to navigate acute 135° angles during certain intralumenal procedures. ERCP (endoscopic retrograde cholangiopancreatography) procedures require such convoluted paths and are becoming much more popular due to the improved patient outcomes derived through this technique. The procedure requires considerable flexibility, and considerable device length. However, with standard flexible materials, the longer the device is, the less "pushability" it will have at the tip of the device. Specifically, current technology makes use of conventional devices very difficult or impossible for ERCP. Current technologies are either too rigid to approach the desired target areas, or too flexible to effect any force transmission to the distal tip if they do achieve the target site. There are no known technologies that allow a material to be "tunable" with both good flexibility and good pushability within the desired portions of the same device, or flexibility in the desired place of flexibility.

Current patented technologies also describe only very simplistic relief notches that are in no way customized or engineered to allow variability in material performance, and provide only static flexibility. For instance, the medical device described in U.S. Pat. No. 6,419,641, may be too flaccid upon exiting the curved introducer to penetrate and obtain an adequate tissue core specimen in a "hardened" sclerotic liver. Conversely, the distal tip of said device may be too rigid to traverse a tighter than normal curve in the introducer as may be required from time to time. More importantly, the Mark '641 patent is completely "static" in its operation, in that the flexibility designed into the device occurs only at one location, and in one plane. Thus, it actually teaches away from the dynamic flexibility enabled by the instant invention. Similarly the device disclosed in U.S. Publication No. 2004/0133124 to Bates, et al teaches away from the concept of "tunable" flexibility. The device described in Bates defines notches in the cannula and stylet that "face in the same direction" to allow flexibility in only one plane, namely "the plane perpendicular to the plane of the notch." Thus, again, flexibility is not turnable, it is located only at a given device location and is only in one place. The Roth device design manufactured by Cook is compliant and flexible enough, but does not transfer cutting energy to the distal tip effectively enough to obtain adequate biopsy samples. Conventional fine needle aspiration devices also suffer from a similar lack of effectiveness in transferring force for penetrating the surface of the target area. Forceps designed for tissue removal/retrieval also are unable to penetrate beneath the surface of the target site in many instances.

Accordingly, there is a need among physicians for devices that can traverse contorted/curved introducers and endoscopes while maintaining the option of a maximum amount of tip rigidity and pushability in the distal and other segments of the device, as needed, and is adaptable to numerous procedures, such as biopsies of the pancreas and bile duct, or of "hardened" or sclerotic liver. There is a further need for a technology that allows for such a device to exhibit custom tunability of flexibility at specific points along the length of the device.

SUMMARY OF THE INVENTION

The Dynaflex technology described herein can utilize both simplistic and sophisticated notch designs, as determined and custom-engineered for specific applications. Utilizing the technology and methods disclosed, the device characteristics of flexibility and rigidity can be adapted by the physician or device manufacturer according to the type of procedure, the patient size and unique anatomical challenges of a given procedure. Rigidity and flexibility can be actively controlled by the operator at predefined portions of a device through rotating the stylet within the cannula to bring about alignments of customized notches to impart target flexibility or rigidity profiles at specific spots on the device. This alters the relationship and orientation of specific notched and non-notched segments of either or both the stylet and cannula that are strategically located at said critical points along the length of the device.

BRIEF DESCRIPTION OF THE DRAWINGS

FIG. 1 depicts a prior art stylet (or wire) side/front views and planes of maximum flexibility and maximum rigidity.

FIG. 2 depicts a prior art cannula (or tubing) side/front views and planes of maximum flexibility and maximum rigidity positions.

DETAILED DESCRIPTION OF THE INVENTION

Figure 3:
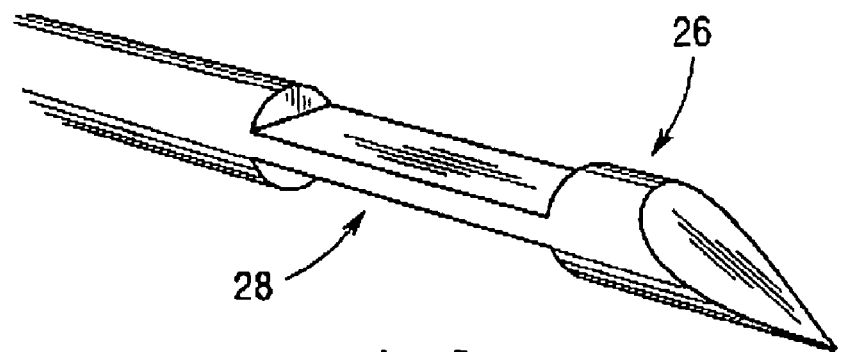
FIG. 3 depicts a double notched stylet as one embodiment of the instant invention.

The present Dynaflex technology enables intralumenal medical access devices to exhibit previously unheard of control over flexibility and pushability at pre-designated portions of the instrument. The technology allows the device operator to custom tailor the flexibility and rigidity of given sections of devices through rotational, axial alignment, and manipulation of the orientation of the stylet to the cannula to each other.

As used herein, the term "cannula" refers to any outer component of a device such as a coaxial device, and specifically including an outer hollow needle, typically stainless steel, but capable of being manufactured with other materials. The cannula has a cannula wall, ordinarily with a thickness of between about 0.003" and 0.200", a distal end, a proximal end, and is designed to accept an inner needle with an maximum outer circumference equal to or less than the minimum inner diameter of the cannula.

As used herein, the term "stylet" refers to any inner component of a coaxial device, and specifically including a "wire" or needle that is slidable within a corresponding cannula, with a proximal end, a distal end, and with a functional end or tip that is designed to perform or assist in a designated medical procedure. This can include, for example, cutting a small biopsy sample, and can also include a hollow needle or "inner cannula," such that it could penetrate and retrieve a target sample. For such hollow needle uses, the most desirable gauges for the majority of medical uses would be about 18, 19 or 20, however the disclosed technology can be utilized with any gauge.

As used herein, the term "intralumenal device" refers to any multiple coaxial devices, including but not limited to a notched stylet and cannula set, a tube within a tube, or other component devices that comprise two or more coaxial components that can be used in medical treatment or diagnosis.

As used herein, a "notch set" is either a cannula notch set or a stylet notch set. The depth of the notch set can be partial, or it can penetrate the full dimension of the device component. Where there is such penetration, it may be necessary to include inner cannula sheaths or coatings to seal the penetrations to ensure the ability of the device to aspirate under vacuum, or to otherwise extract the sample or specimen. Such coatings can be polymeric in nature, allowing flexibility and the necessary seal, and are well known to those skilled in the art.

As used herein, the term "cannula notch set" refers to a series of one or more notches or etchings and the corresponding unetched or un-notched areas, occurring approximately at a fixed point along the length of the cannula which can be of equal length and/or equidistantly axially spaced but can also be of varying length and spacing.

As used herein, the term "stylet notch set" refers to a series of one or more notches and the corresponding unnotched areas, occurring at fixed points along the length of the stylet which can be of equal length and/or equidistantly axially spaced, but can also be of varying length and spacing.

Figure 4A:
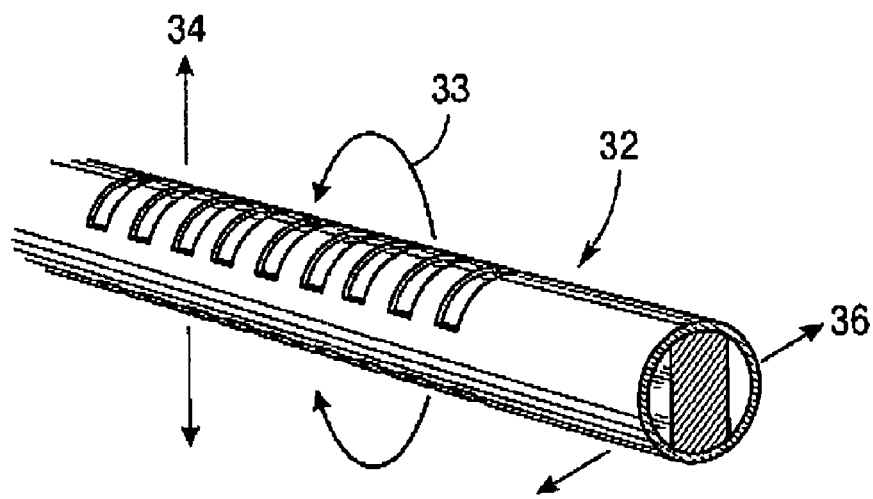
FIG. 4 depicts cross sections of the cannula in conjunction with the stylet of the subject invention inside oriented for both maximum flex and maximum rigidity positions.
Figure 4B:
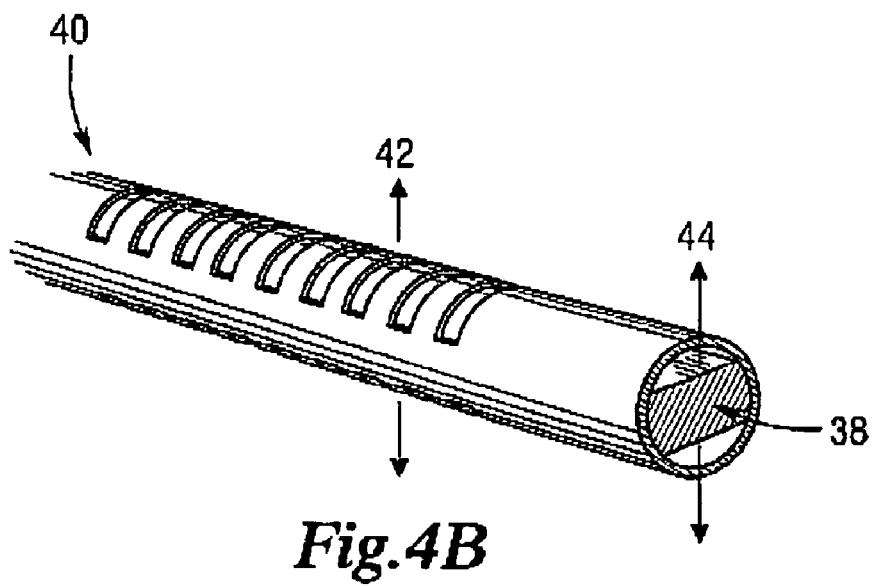

As used herein, "radial alignment" refers to a point at which the centerpoint of a cannula notch is aligned with either the centerpoint of a stylet notch or the centerpoint of its un-notched segment, as depicted in FIGS. 4A and 4B.

As used herein, "linear alignment" means a point along the functional linear length of the device wherein any stylet notch set and any cannula notch set are aligned.

The subject invention relies upon a novel dynamic orientation between the custom engineered stylet and cannula components in order to vary the flexibility and/or rigidity in given section(s) of the intralumenal device. As one example, the distal tip section of a device with notch sets as depicted in FIG. 5 can be made more flexible by the operator where the stylet and cannula notch sets are in radial alignment, such as depicted in FIGS. 4A and 4B, to accommodate tip deflection of the scope or introducer. As the intralumenal device tip protrudes from the scope or introducer, the exact same segment of the device tip can be made by the operator to become more rigid by rotating the stylet 90° within the cannula, so that the initial segment becomes rigid, as depicted in FIG. 4A, and thereby causing this first section to transform from flexible to rigid, and a second section to transform from rigid to flexible, as depicted in FIG. 4B. In this fashion, the tip becomes rigid, while the subsequent distal section is made more flexible in order to accommodate passage through the deflected scope/introducer. This is only one simple example of a flexibility profile for a device that can be designed utilizing the design and engineering methods, and the materials of the subject invention. These features have specific application for endoscopic, bronchoscopic and laparoscopic biopsy, for example.

In simplest terms, the operator of an intralumenal device utilizing the subject technology can make a section of the device alternatively rigid or flexible in real time as it transverses the introducer/scope. The lead section can be more flexible to transverse the deflected scope tip while the following section is more rigid to allow pushing/force transmission from the proximal end. By the operator simply rotating the stylet of the described device 90° within the cannula, the reverse occurs: the lead section becomes more rigid as it protrudes from the scope, and the following section becomes more flexible to accommodate the deflection of the scope.

Multiple relief notches or etchings, comprising "notch sets" are positioned perpendicular to the longitudinal axis of the device. As one basic embodiment, these notches within a notch set of a cannula initiate at 0° and 180° and involve an arc of less than 180°. Preferably, the radial arc of the notches is between about 30° and 120°, thereby resulting in perpendicular sections within a notch set of about 1500 and 60° remaining solid and "unnotched." The stylet relief notch set(s) in the distal section is oriented at the 180° position for greatest flexibility, wherein the notch set(s) at that area are in radial alignment. The stylet is then rotated 90° by the operator to realize maximum rigidity for the distal section, wherein the notch sets are perpendicular to this radial alignment. The next section of the stylet has a relief notch perpendicular to the lead distal section. This allows the second section to be out of phase with the first section and the cannula etchings.

Figure 8A:
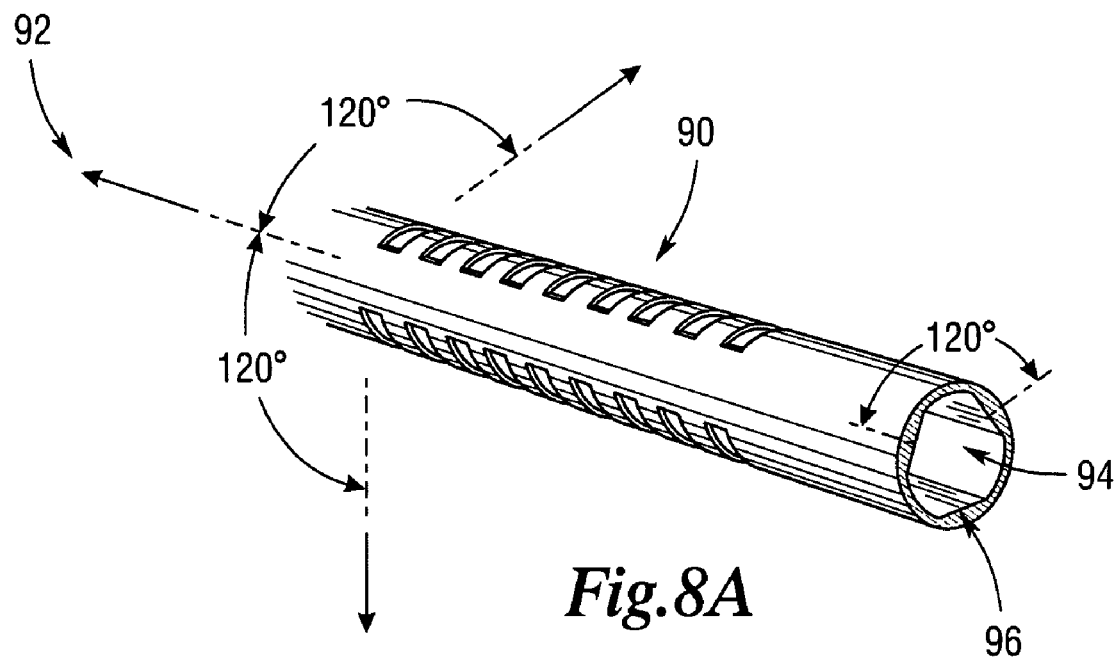
FIG. 8 depicts alternative notch sets at 120° radially, and with one 330° notch set.
Figure 8B:
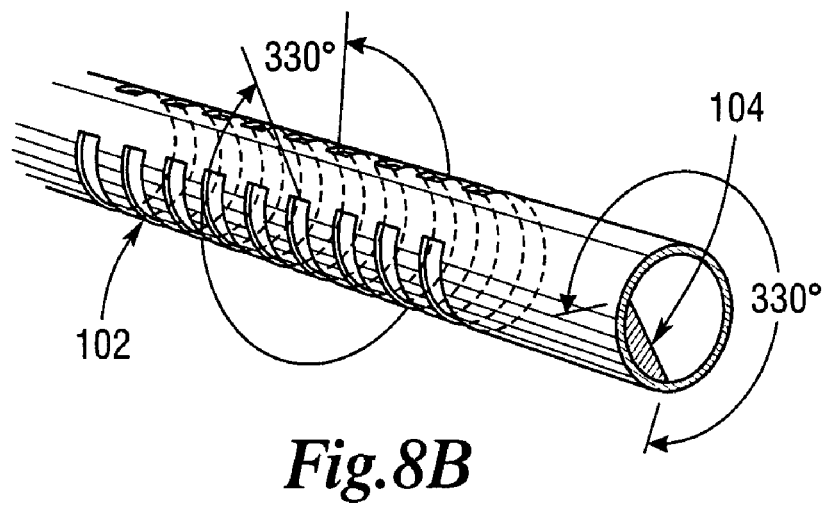

Utilizing methods disclosed herein, the device designer or operator can "map" the flexibility profile(s) required for a given procedure. By "mapping" alternating sections of the length of a device component with notch set(s) of varying axial orientation, and varying degrees of flexibility and pushability, the instrument can be designed to exhibit customized and controlled characteristics at and along unique portions of the instrument. The amount of flexibility and pushability can be carefully engineered and controlled at the time of design for a particular intralumenal device. By controlling the arc length of the notch sets, the frequency and the location of notch sets, transitions, the degree of phase change, and the notch dimensions, a broad range of flexibility can be "tuned" into the device by its operator, during a procedure. The shorter the arc of the notch, the less flexibility the device will exhibit at that point of radial alignment. However, as depicted in FIG. 8B, the arc can be up to 330°, which will impart significant flexibility to that particular device segment.

Although numerous techniques can be used in order to create the slots or notches necessary to impart the desired flexibility, one preferred method is the laser assisted micro-machining technology currently developed and utilized by Creganna Medical Devices, Ireland (the "Creganna technology"). In the Creganna technology, the cannula has custom designed slotting, both as to the axial arc radius of the slots, the longitudinal spacing of the slots, and the width of the slot itself.

The inventor has developed a prototype device, manufactured in part by Creganna Medical Devices to the following specifications.

Inner diameter of cannula of about 0.90 mm
Stylet outer diameter of about 0.866 mm
160 mm laser cutting radius about 10 mm This cannula and stylet set could be used for:
Tissue removal/sampling
Device implantation (Stent, radioactive seeds)
Foreign object removal
Therapeutic procedures—angioplasty, sutures The major benefits of this technology over any other existing technology include the ability to dynamically control the flexibility and rigidity characteristics of given segments through convoluted difficult passages and transmission of necessary mechanical energy from the proximal device to the distal tip without compromising flexibility at the points along the length of the device.

Maximum flexibility of the device or a portion of the length of the device is achieved when the center point of a cannula notch set is aligned with the center point of the corresponding stylet notch set. Alternatively, maximum rigidity of the device is achieved when the center point of a cannula notch set is in line with the center point of the non-notched, rigid sections corresponding to the stylet notched set. This relationship holds true regarding both flexibility and rigidity, regardless of the number of slotted regions and the length of the slots. As indicated in FIG. 8A, it is not essential for the notch sets to be oriented at 180°. They can be oriented at 120°, or other unique geometries that will be apparent to one skilled in the art.

Moreover, various gradations of flexibility and device characteristics can be achieved as the device is "tuned" by rotating the stylet from the point of radial alignment through to the point where the centerpoint of a stylet notch is furthest away from the centerpoint of the notch(es) contained in the stylet.

The invention also allows for an unexpected operating characteristic. This characteristic involves the inherent "steerability" of the intralumenal device.

Because the device has dynamic flexibility with axial rotation, when the catheter tip encounters resistance, the resistance translates to torque on the length of the device, and this torque causes the stylet to rotate axially within the cannula at the point of resistance, thereby causing an increase and an automatic adjustment of flexibility where the rotation brings notch sets closer to radial alignment. Thus, this intralumenal resistance automatically brings about a change in flexibility at that point. These dynamic and varying characteristics can be used by the operator to navigate and to even "steer" the device as it progresses through an intralumenal procedure. For many medical devices applications, two regions with notches, as depicted in FIG. 5, are desirable. However, other configurations are possible. For instance, where notch sets consist of three notches, instead of two, device flexibility is directly impacted in three directions, maximally at 120° radially. As depicted in FIG. 8A, notches oriented at 120°, allow a device to be maximally flexible in three different planes, and with a different flexibility profile than if the notches were oriented at 180°.

Importantly, the notch set can also consist of one notch. This notch can be as great as 330°; however, a preferred range for single slotted notch set is between about 180° and 300°. A single notch set of 330° is depicted in FIG. 8B.

DETAILED DESCRIPTION OF THE DRAWINGS

FIG. 1 depicts a prior art stylet, 10. The stylet contains a cut out notch, 12, which allows the stylet flexibility in one plane, 14, that is perpendicular to the radius of the notch cut marked A and allows the stylet greater flexibility in that plane, but retaining rigidity in field of motion of the opposite plane, 16, motion.

FIG. 2 depicts a prior art cannula, B. The cannula contains notch sets, 20, machined into its surface that allow the cannula greater flexibility in one plane, 22, marked A that is parallel with the centerpoints of the matched areas of the notch set, 24, but retaining rigidity in the perpendicular field of motion marked "B." When the stylet, 10, is used in conjunction with the cannula, 18, there is maximum flexibility only in one plane of motion.

FIG. 3 depicts a double notched stylet, representing an embodiment of the instant invention. The stylet, 26, has two machined notches, 28, imparting flexibility into the stylet in one direction, at the point of the notches. It is not necessary to practice the invention for the stylet to contain double notches. Similarly, it is not necessary for the cannula depicted in FIG. 4 to have mirror image notches. In fact, in many instances, a single notch can suffice. The depth of the notch can preferably be more than 50% of the cross section of the stylet, and can be up to 90% or more, so long as there remains sufficient material to provide pushability and integrity of the stylet at the point of the notch.

FIG. 4 depicts the dynamic flexibility range of the instant invention. FIG. 4A depicts a cross section of a cannula/stylet set wherein the cannula, 32, contains two notched sections, 33, on opposite sides of the cannula. In FIG. 4A, the plane of flexibility of the cannula, 34, is perpendicular to the plane of flexibility of the stylet, 36. This results in an orientation of stylet and cannula that is minimally flexible. However, as depicted in FIG. 4B, where the stylet, 38, is rotated within the cannula, 40, 90°, so that the planes of flexibility, 42 and 44, are parallel, and thus in radial alignment, the same stylet and cannula can exhibit a profile of maximum flexibility. It is not necessary that the cannula contain two sets of diametrically opposed notches; if the notch is sufficiently large in radius, one notch can impart a sufficient degree of flexibility when the stylet is in axial alignment.

Figure 5A:
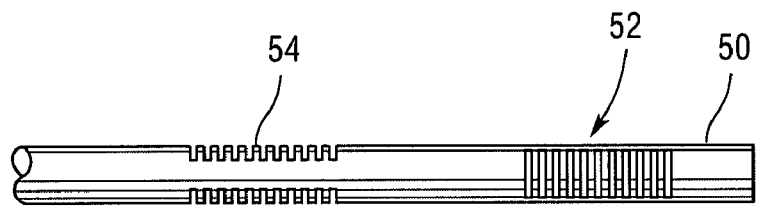
FIG. 5 depicts custom notch sets that simultaneously allow tuned flexibility in different planes.
Figure 5B:
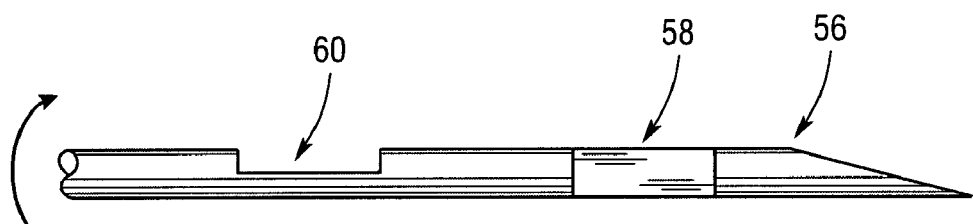
Figure 5C:
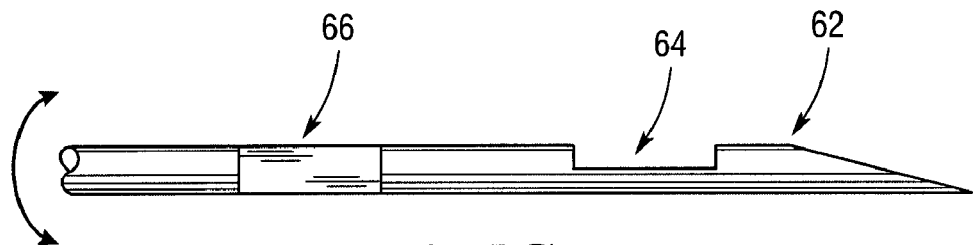

FIG. 5 depicts a cannula and notch set that allows a single set to demonstrate customized flexibility in different planes, at different points along the length of the cannula. The cannula of FIG. 5A, 50, contains two notch sets, 52 and 54, that allow flexibility in planes perpendicular to each other. The stylet, 56, in FIG. 5B depicts two notches, 58 and 60, that, when inserted into the cannula in the orientation depicted in FIG. 5A, results in maximum flexibility at both points of flexibility. However, the stylet depicted in FIG. 5C, 62, when inserted into the cannula oriented as depicted in FIG. 5A, would result in a profile of maximum rigidity at the points of both notches, 64 and 66. Importantly, the cannula/stylet set flexes in one plane of direction at one notch set, 52, and simultaneously in another direction at the second notch set, 54, when the corresponding notch sets are in lineal alignment. As the stylet is advanced, the stylet's first initial notch 58 and 64, first encounters the cannula notch, 54, and depending upon its radial orientation, is either flexible or rigid at that position.

Figure 6:
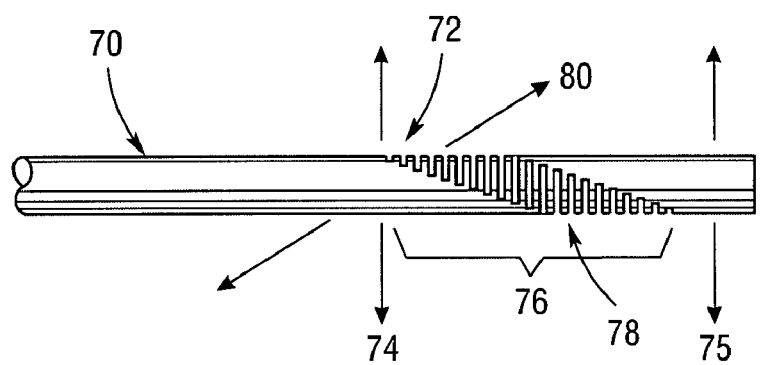
FIG. 6 depicts a dynamically flexible transition profile of a cannula.

FIG. 6 depicts a further customization of flexibility. When utilizing the methods of device design disclosed herein, a cannula, 70, can contain notch sets that progressively shift along the length of the cannula from one plane of flexibility, as at notch set, 72, which allows flexibility in one plane, 74, through the length of the catheter, 76, and transitioning at a point along that length, 75, to a plane of flexibility, 80, perpendicular to the initial plane, 74. As the stylet depicted in FIG. 4A is passed through the cannula depicted in FIG. 6[A]0 at the same radial orientation, the flexibility profile in a given plane will progressively change, as the operator advances the stylet through the cannula, achieving different points of linear alignment.

Figure 7:
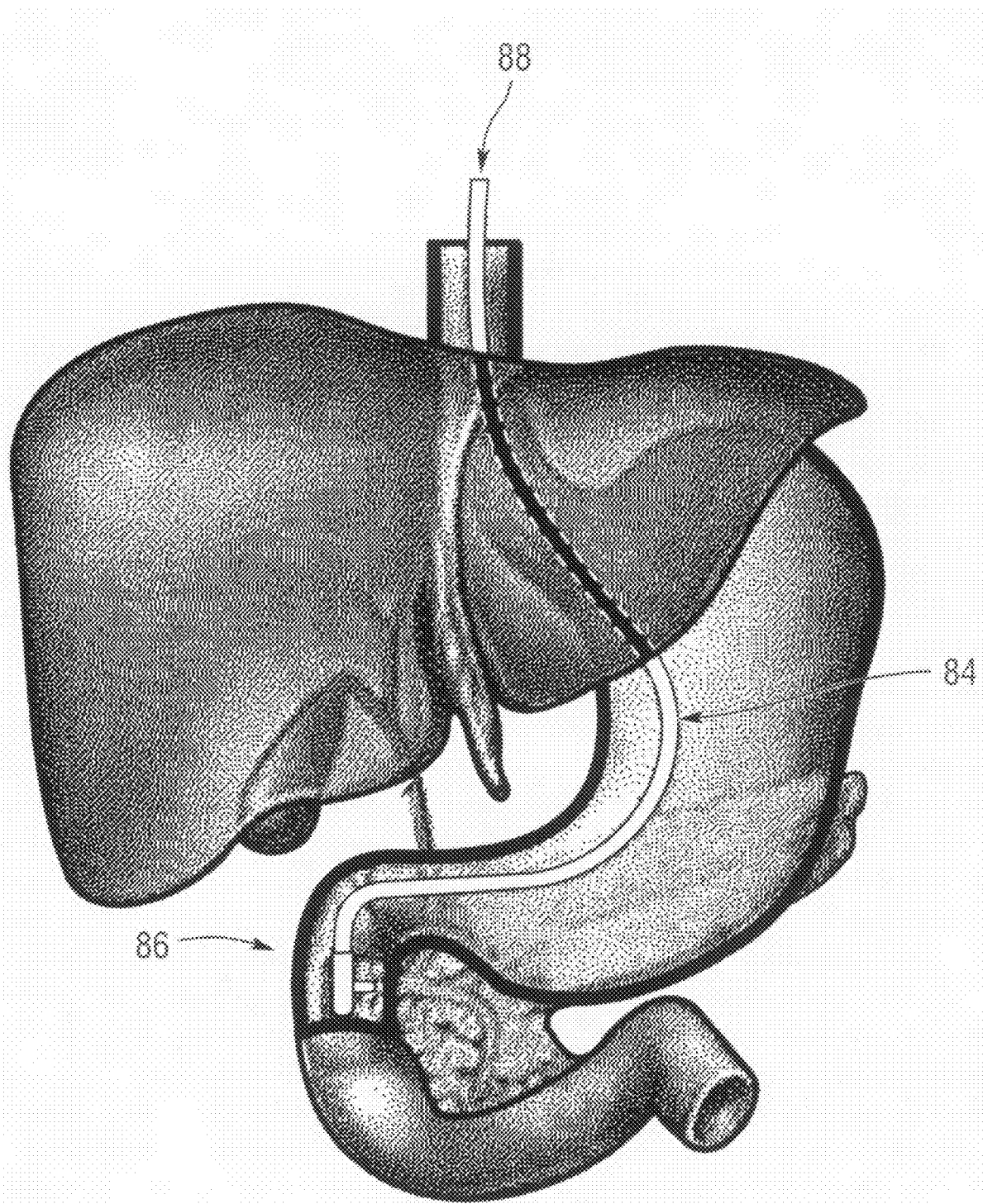
FIG. 7 depicts the human anatomical required path of an intralumenal medical device to perform an ERCP.

FIG. 7 depicts a cross sectional anatomical view of the path of an intralumenal device necessary to perform an ERCP procedure. As depicted, the device, 84, is required to navigate significant bends and turns as it advances through the patient. At some locations, the device must conform to a 135° bend, 86. In addition, the device must be rigid, with good pushability, at the point of introduction, 88.

FIG. 8 depicts two examples of what may be an infinite number of custom engineered alternative notch sets that will impart their own unique and custom flexibility and pushability profiles at those specific points of radial and/or lineal alignment along the length of an intralumenal device. FIG. 8A shows a notch set with three sets of cannula notches, 90 for which the center points are 120° apart. This allows for maximum flexibility in three separate planes, 92, as a stylet, 94 with three machined notches, 96, is axially rotated. FIG. 8B depicts a single notch set, with one cannula notch, 102, and one stylet notch, 104. When aligned at a point of radial alignment, the device exhibits maximum flexibility at that point of the device and at varying degrees of flexibility at other points of alignment, such as the point depicted in FIG. 8B.

Figure 9:
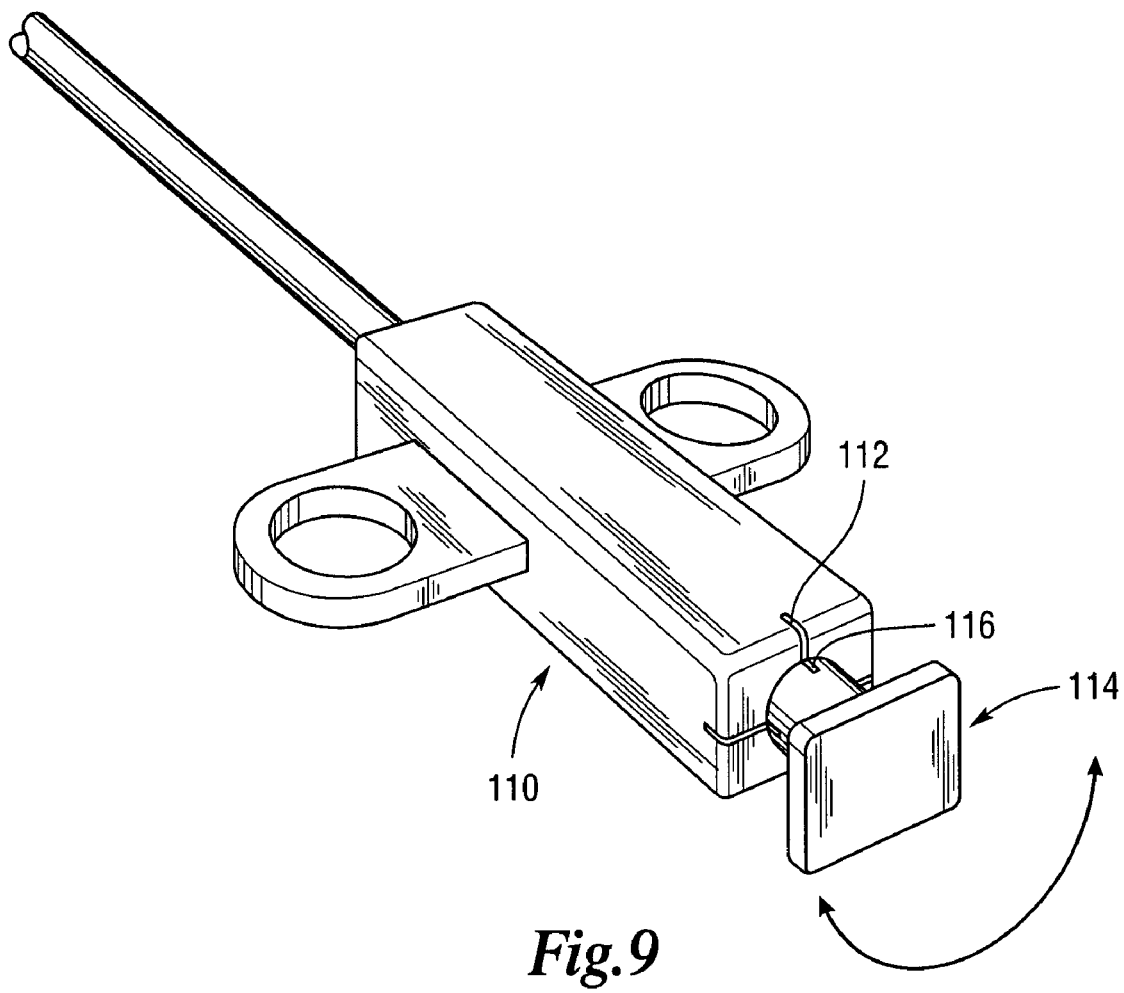
FIG. 9 depicts an operator's handle with rotation demarcations.

FIG. 9 depicts a view of an embodiment of the invention wherein the operator's handle, 110, contains reference demarcations, 112, as a reference to measure against similar demarcations on the stylet control, 114. As the stylet is axially rotated in either direction by the operator, as indicated, the demarcations on the stylet control, 116, can be referenced against the base handle, 110, to determine the orientation of the stylet to the cannula. Thus, at any predetermined point along the length of the device, flexibility can be specifically tuned into the device.

The number and length of the sections with cannula or stylet notch sets can be adjusted to accommodate specific applications. This concept can also be used for applications such as vascular access, guide wires, GI and pulmonary procedures.

Between any of said customized sections of a device, there can also be a transitional alignment to accommodate the advancement of the device from one section to another. One embodiment of such approach is to utilize circumferential grooves in the transitional area to allow deflection in multiple planes but which are still adequate to transfer necessary force to the distal tip. An example of such a transition configuration is depicted in FIG. 6.

The inventor also discloses herein a method for the design and fabrication of a tunably flexible intralumenal medical device. The method comprises the steps of identifying a medical procedure that involves the introduction of an intralumenal device into an intralumenal passage. It is then determined the approximate internal route within the body, including the nature and extent of bends the device will be required to navigate in order to reach the point of care or treatment for the device. This can, in certain circumstances, involve at least two or three important bends. The bends can involve simultaneous different planes of flex at different sections of the device. Utilizing the novel technology described herein, a device specific to that procedure can be developed which includes customized flexibility and/or pushability that can be "created" by the device operator during the procedure at predetermined points along the medical device that correspond to the median placement of bends or device geometries presented by the anatomy of a statistically average patient undergoing the procedure in question. An example of such a customized medical device would be one designed to perform an ERCP biopsy, as depicted in FIG. 4.

Mathematical models are then utilized to optimize or "map" the geometry of each of the components as well as the overall device for specific applications where there is such a need for adaptation of rigidity and/or flexibility. This method allows for the successful development of optimal custom designs for numerous medical devices where such needs are vital.

The flexibility and pushability "mapping" for a specific procedure typically requires an operator to establish pre-set axial stylet and cannula orientations at specific points along the length of the intralumenal device. Such length markers would be clearly visible to the operator. The axial orientation would be defined, preferably, on the introducer portion of the device, or on the handle, as depicted in FIG. 9. In various embodiments, the axial orientation can be correlated with corresponding demarcations along the length of the intralumenal device. Other methods of demarcating positions along the length of the device to alter the radial alignment of the device components, including the use of electronic means, are well known to those skilled in the art. These can include optical markers, or utilization of embedded piezoceramics to signal a particular radial alignment at a point of linear alignment.

Finally, although the desired technology is uniquely suited for the design and manufacture of custom intralumenal medical devices, the technology and methods disclosed herein can also be suitably employed to design devices for industrial and other applications. For instance, custom flexibility may be required in an underground petroleum or gas well setting.

Maintenance devices for pipes in nuclear facilities often require custom flexibility. Through utilization of a two piece mechanism with notch sets as described herein, such industrial devices may be designed to navigate very acute angles within pipes and fixtures, without compromising the push-ability or effectiveness of the working end of the device.

While the present teachings have been particularly shown and described with reference to various embodiments thereof, it will be understood by those skilled in the art that various alterations in form and detail may be made therein and various applications employed, without departing from the spirit and scope of the invention.

What is claimed is:

1. An intralumenal medical access assembly featuring dynamic variable degrees of flexibility controlled in real time during a medical procedure, comprising:
   (a) a cannula with at least one cannula notch set along its length; and
   (b) a stylet having a length greater than about 50 mm with at least one stylet notch set along said length;
      wherein said stylet is both longitudinally slideable within and radially rotatable within, said cannula at any position along a functional linear length of the cannula,
      and wherein at one or more points of longitudinal alignment along said cannula functional linear length, the stylet notch set is radially rotatable to a degree of radial alignment with at least one cannula notch set, said radial alignment causing a variable flexibility of the assembly at the point of alignment.

2. The assembly of claim 1 wherein the cannula notch set has a total arc length in the range of about 30° to 330° of the circumference thereof.

3. The assembly of claim 1, wherein the notch sets are machined through laser machining techniques.

4. The intralumenal medical access assembly of claim 1, wherein the cannula further includes a polymer sheath or coating on its interior surface.

5. An intralumenal medical access assembly featuring dynamic variable degrees of flexibility controlled in real time during a medical procedure, comprising:
   (a) a cannula with at least one cannula notch set along its length; and
   (b) a stylet having a length greater than about 50 mm with at least one stylet notch set along said length;
      wherein said stylet is both longitudinally slideable within and radially rotatable within said cannula at any position along a functional linear length of the cannula,
      and wherein at one or more points of linear alignment, the stylet notch set is radially rotated through 360° of rotation, thereby causing a gradation of flexibility and rigidity as the stylet notch set moves toward and away from a point of radial alignment, said radial rotation causing a variable change in flexibility of the assembly.

6. An intralumenal medical access assembly having longitudinal flexibility in two or more planes, comprising:
   (a) a cannula with at least two cannula notch sets along its length; and
   (b) a stylet having a length greater than about 50 mm with at least one stylet notch set along said length;
      wherein said stylet is both longitudinally slideable within and radially rotatable within said cannula at any positions along its functional linear length,
      and wherein said stylet notch set is flexible in a first plane at a point of radial alignment with a first cannula notch set, and upon radially rotating and advancing the stylet, is flexible in a second different plane at a second point of linear alignment and radial alignment at the second notch set.

7. An intralumenal medical access assembly having longitudinal flexibility in two or more planes, comprising:
   (a) a cannula with at least one cannula notch set along its length; and
   (b) a stylet having a length greater than about 50 mm with at least one stylet notch set along said length;
      wherein said stylet is both longitudinally slideable within and radially rotatable within said cannula at any positions along its functional linear length,
      and wherein a stylet notch set is flexible in a first plane at a point of radial alignment with a first cannula notch set, and upon radially rotating and advancing the stylet, is flexible in a second different plane at a second point of linear alignment and radial alignment at the second notch set.

8. A method for the design and fabrication of an intralumenal device having variable flexibility, comprising:
   (a) identifying an intralumenal medical procedure;
   (b) mapping required flexibility and pushability requirements encountered during introduction and advancement of an intralumenal device to perform the procedure; and
   (c) designing a device with notch sets strategically located to allow flexibility and pushability in two or more planes to be tuned into the device at the mapped points;
   (d) wherein variable flexibility of said device is achieved through radial rotation of a stylet within a cannula at one or more longitudinal points of the cannula.

9. The method of claim 8, further comprising the step of machining the notch sets using laser machining technologies.

10. The method of claim 8, wherein said variable flexibility design allows flexibility in a first plane at a point of radial alignment with a first cannula notch set, and upon radially rotating and advancing the stylet, also allows flexibility in a second, different plane at said second point of linear alignment and radial alignment at a second notch set.

11. An intralumenal medical access assembly featuring dynamic variable degrees of flexibility controlled in real time by an operator, comprising:
   (a) a cannula with at least one cannula notch set along a length thereof; and
   (b) a stylet having a length greater than about 20 mm with at least one stylet notch set along said length;
   the intralumenal medical access assembly comprising a rigid alignment when a central point of at least one cannula notch set is aligned with a central point of a non-notched section of said stylet.

* * * * *